United States Patent [19]

Katsura

[11] Patent Number: 4,690,762
[45] Date of Patent: Sep. 1, 1987

[54] APPARATUS FOR REMOVING BUBBLES FROM A LIQUID

[75] Inventor: Yoshiro Katsura, Narashino, Japan

[73] Assignee: Terumo Kabushiki Kaisha, Tokyo, Japan

[21] Appl. No.: 854,679

[22] Filed: Apr. 18, 1986

Related U.S. Application Data

[63] Continuation of Ser. No. 618,058, Jun. 7, 1984, abandoned.

[30] Foreign Application Priority Data

Jun. 10, 1983 [JP] Japan ................ 58-102726

[51] Int. Cl.$^4$ ............................................. B01D 19/02
[52] U.S. Cl. .................................... 210/436; 210/457; 210/472; 210/497.3; 210/512.1; 55/178
[58] Field of Search ............... 210/218, 304, 305, 306, 210/308, 309, 420, 422, 456, 457, 497.01, 497.3, 512.1, 782, 927, 540, 188, 436, 472; 55/159, 178, 185, 190

[56] References Cited

U.S. PATENT DOCUMENTS

| | | | |
|---|---|---|---|
| 3,701,433 | 10/1972 | Krakauer et al. | 210/927 |
| 3,827,562 | 8/1974 | Esmond | 210/304 |
| 4,056,476 | 11/1977 | Mouwen et al. | 210/927 |
| 4,087,363 | 5/1978 | Rosemeyer et al. | 210/927 |
| 4,111,829 | 9/1978 | Bimond et al. | 55/178 |
| 4,126,558 | 11/1978 | Luceyk | 210/927 |
| 4,157,965 | 6/1979 | Raible | 210/927 |
| 4,283,289 | 8/1981 | Meyst et al. | 210/927 |
| 4,401,566 | 8/1983 | Igari et al. | 210/927 |
| 4,411,783 | 10/1983 | Dickens et al. | 210/927 |
| 4,490,254 | 12/1984 | Gordon et al. | 210/927 |
| 4,493,705 | 1/1985 | Gordon et al. | 210/927 |

FOREIGN PATENT DOCUMENTS 163372  9/1983  Japan .

Primary Examiner—Richard V. Fisher
Assistant Examiner—Wanda L. Millard
Attorney, Agent, or Firm—Frishauf, Holtz, Goodman and Woodward

[57] ABSTRACT

Apparatus for removing bubbles from a liquid such as blood, includes a conically shaped filtration member disposed in a cylindrical vessel and coaxial therewith. The filtration member divides the space in the vessel into an upper space and a lower space. The vessel has a liquid inlet port positioned at the same level as the upper end of the filtration member and a liquid outlet port through which the treated liquid is discharged. A gas outlet port is provided in the wall of the vessel in communication with the upper space.

7 Claims, 10 Drawing Figures

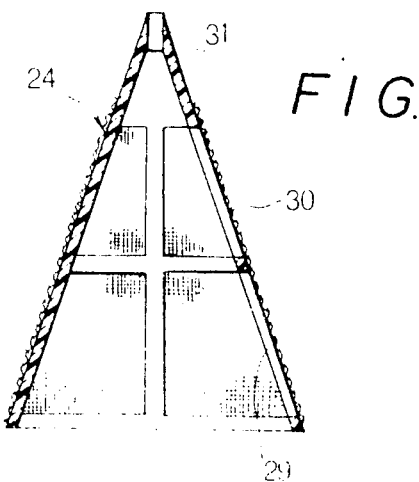
FIG. 6
FIG. 7
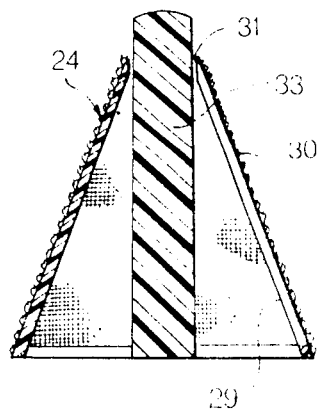
FIG. 8
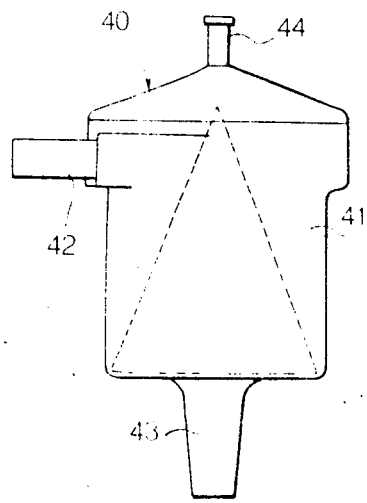

APPARATUS FOR REMOVING BUBBLES FROM A LIQUID

This application is a continuation of application Ser. No. 618,058, filed June 7, 1984, now abandoned.

BACKGROUND OF THE INVENTION

1. Field of the Invention

The present invention relates to an apparatus for removing bubbles from a liquid having a medical use. More particularly, the invention is concerned with an apparatus for removing bubbles from a liquid such as blood flowing in an extracorporeal blood circuit of artificial organs, e.g., an artificial lung, artificial kidney, separator for separating blood plasma from blood cells, and so forth, and the dialysate which flows in a dialysis circuit in an artificial kidney.

2. Description of the Prior Art

There are three types of apparatus for removing bubbles from a liquid. These are an apparatus of filtration type, an apparatus of settling type, and an apparatus which makes combined use of both the filtration type and settling type.

The apparatus of filtration type usually employs a filter having a pore size of 20 to 45 microns or a screen having a mesh size of 180 to 200 microns. The filter, however, produces a large pressure loss and tends to damage the constituents of blood, while the screen often fails, inconveniently, to trap minute bubbles.

In the apparatus of the settling type, as well as the apparatus which simultaneously uses both the filtration type and settling type, a blood reservoir of a large volume is employed, in which the blood is temporarily stored to allow the bubbles to be separated by buoyancy. In such apparatus, it is possible to remove fine bubbles to some extent, provided that the volume of the reservoir is sufficiently large. The large reservoir volume, however, increases the quantity of blood for priming, i.e., for filling up the reservoir. Consequently, the quantity of blood or other similar liquid for transfusion, as well as the quantity of residual blood or liquid after circulation, is increased. This results in various troubles.

Under these circumstances, there has already been proposed, in the specification of Japanese Provisional Patent Publication No. 58-163372, an apparatus for use in a blood circuit which is capable of removing even fine bubbles from the blood, while diminishing the quantity of blood required for priming and minimizing the pressure loss caused by the filter. More specifically, this proposed apparatus has, as shown in FIG. 1, a vessel 2, a planar filtration member 3 disposed in the vessel 2 so as to divide the space in the vessel 2 into an upper space and a lower space, a liquid inlet port 4 provided in the wall of the vessel 2 for communication with the upper space and adapted to introduce the liquid into the upper space in the form of a vortex flow around the axis of the vessel 2, a liquid outlet port 5 provided in the wall of the vessel 2 for communication with the lower space in the vessel 2 and adapted to allow the treated blood passed through the filtration member 3 to be discharged therethrough, and a gas outlet port 6 provided in the wall of the vessel 2 for communication with the uppermost region of the upper space in the vessel 2 and adapted to allow the separated gas to be discharged therethrough. With this apparatus 1, therefore, the bubbles in the blood are positively separated centrifugally in the outer peripheral region where the velocity of vortex flow is high, while in the central region where the flow velocity is small, the centrifugally separated bubbles are allowed to float so as to be discharged through the gas outlet port. Consequently, it is possible to efficiently remove the bubbles with reduced quantity of liquid for priming.

This apparatus 1, however, suffers from the following disadvantage. Namely, the filtration member 3 having a planar shape offers substantial resistance to the blood flowing therethrough causing problems such as a pressure loss and damage to the blood. To avoid these problems, the filtration member 3 is required to have a diameter, i.e., filtration area, large enough to suppress the pressure loss and the damage to blood. Consequently, the volume of the vessel 2 is increased to require a certain quantity of blood for priming. Thus, there is still a demand for reduction of the quantity of blood for priming.

The apparatus for removing bubbles from liquid, to which the invention pertains, is used not only in the blood circuit but also in the dialysis liquid circuit of an artificial kidney for removing bubbles from the dialysis liquid. Removal of bubbles from the dialysis liquid is necessary because bubbles attaching to the dialysis membrane (wall of hollow fibers) form a dead space, thus lowering the dialysis efficiency, and may enter the human body through any defects in the wall of the hollow fiber.

SUMMARY OF THE INVENTION

Accordingly, an object of the invention is to provide an apparatus for removing bubbles from a liquid, capable of satisfactorily removing even fine bubbles from the liquid, while reducing the pressure loss caused by the filtration member and diminishing the priming volume.

To this end, the invention basically provides an apparatus for removing bubbles from a liquid comprising: a vessel; a filtration member disposed in the vessel and dividing the space in the vessel into a liquid inlet space and a liquid outlet space; a liquid inlet port formed in the wall of the vessel in communication with the liquid inlet space and adapted to introduce a liquid into the liquid inlet space in the form of a vortex flow around the axis of the vessel; a liquid outlet port formed in the wall of the vessel in communication with the liquid outlet space and adapted to allow the treated liquid passed through the filtration member to be discharged therethrough; and a gas outlet port formed in the wall of the vessel in communication with an uppermost region of the liquid inlet space and adapted for allowing the gas of the separated bubbles to be discharged therethrough; wherein the filtration member is a three dimensional structure disposed in the vessel coaxially therewith, an upper end of the filtration member being positioned at the same level as the liquid inlet port.

According to a preferred embodiment of the invention, the filtration member is made of a porous material having a pore size ranging between 50 and 260 microns.

According to another preferred embodiment of the invention, the filtration member is made of a hydrophilic material.

According to another preferred embodiment of the invention, the filtration member is made of a porous material treated beforehand to become hydrophilic.

According to another preferred embodiment of the invention, a pillar is provided in the three dimensional filtration member for reducing the volume thereof.

According to another preferred embodiment of the invention, the filtration member is substantially cylindrical in shape and is provided with a side thereof in a porous material and an upper side thereof with a closing plate having at least one communication port being provided in a peripheral region thereof for allowing communication between a fluid inlet and a fluid outlet.

According to still another preferred embodiment of the invention, the filtration member is substantially conical in shape.

According to a further preferred embodiment of the invention, the filtration member of substantially conical shape is provided at its upper end with a communication port which provides communication between the fluid inlet space and the fluid outlet space.

According to still a further preferred embodiment of the invention, the filtration member of substantially conical shape is provided over its upper end with an eddy-current blocking plate which prevents eddy currents of bubbles formed thereon from entering the liquid outlet space.

The above and other objects, features and advantages of the invention will become clear from the following description of the preferred embodiments when the same is read in conjunction with the accompanying drawings, in which like reference characters designate the same or similar parts throughout the drawings thereof.

BRIEF DESCRIPTION OF THE DRAWINGS

FIG. 6 is a sectional view of a filtration member incorporated in the apparatus of the invention;

FIG. 7 is a sectional view of a modification of the filtration member;

FIG. 8 is a front elevational view of a practical example of the apparatus of the invention for removing bubbles from a liquid.

DESCRIPTION OF THE PREFERRED EMBODIMENTS

Figure 2:
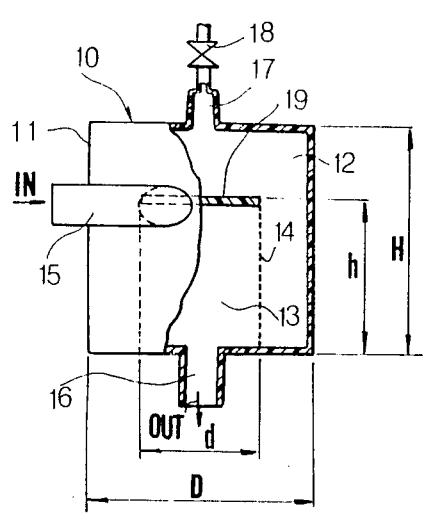
FIG. 2 is a partly-sectioned front elevational view of an embodiment of the apparatus of the invention for removing bubbles from a liquid.
Figure 3:
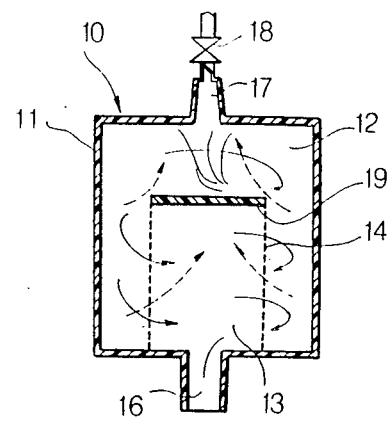
FIG. 3 is a sectional front elevational view of the apparatus shown in FIG. 2.

FIGS. 2 and 3 show a first embodiment of the apparatus 10 of the invention for removing bubbles from blood. The apparatus 10 has a vessel 11, a filtration member 14 made of a porous material and disposed in the vessel 11 so as to divide the space in the vessel 11 into an upper space 12 serving as an inlet space and a lower space 13 serving as an outlet space, a liquid inlet port 15 formed in the wall of the vessel 11 for communication with the upper space 12 and adapted to introduce the blood to be treated into the upper space 12 in the form of a vortex flow around the axis of the vessel 11, a liquid outlet port 16 provided in the wall of the vessel 11 for communication with the lower space 13 and adapted to allow the treated blood which passes through the filtration member 14 to be discharged therethrough, and a gas outlet port 17 provided in the wall of the vessel 11 for communication with the upper most region of the upper space 12 and adapted for discharging the gas of the bubbles separated in the upper space 12. A valve 18 is connected to the gas outlet port 17.

The filtration member 14 has the form of a vertical cylinder concentric with the axis of the vessel 11. The entirety of the cylindrical surface of the filtration member 14 is constituted by a mesh. The liquid inlet port 15 is disposed substantially at the same level as the upper end of the filtration member 14. A closure plate 19 is fixed integrally to the top end of the filtration member 14. The closure plate 19 effectively prevents the vortex flow of blood thereon from entering the lower space 13.

Figure 4:
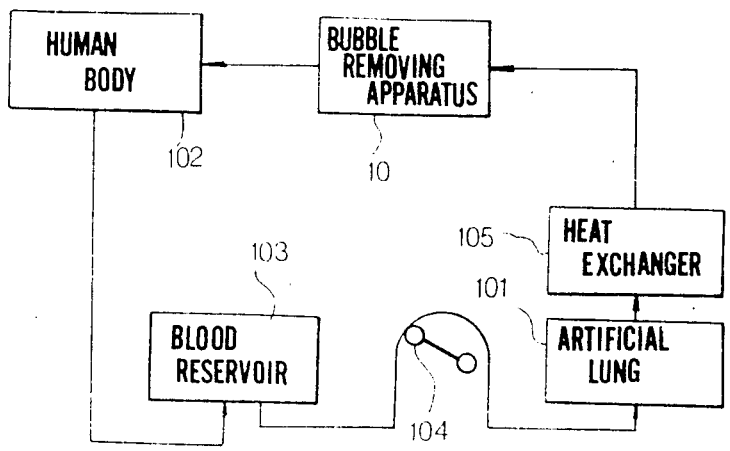
FIG. 4 is a circuit diagram of an artificial lung.

This apparatus 10 is used, for example, in an artificial lung system as shown in FIG. 4. In this case, the apparatus 10 is connected at a location downstream of an artificial lung 101 and upstream of the human body 102 as viewed in the direction of flow of the blood, but very close to the human body 102. The heart and lung machine has a blood reservoir 103, pump 104 and a heat exchanger 105. The apparatus 10 is primed with physiological saline, lactic Ringer's solution or a similar liquid, before it is charged with the blood to be treated. It is desirable to provide a communication hole in a peripheral region of the closure plate 19 in order to communicate the upper space 12 and the lower space 13. Then, the blood to be treated is introduced through the liquid inlet port 15 into the upper space 12 to fill up the latter and flows therein in the form of a vortex flow. The vortex flow of the blood in the upper space 12 of the vessel 11 is progressively moved from the peripheral portion to the central portion of the upper space 12. In the outer peripheral zone of the vortex flow of the blood where the velocity of flow of the blood is comparatively high, the bubbles and the blood, having different specific gravities, are separated from each other by the action of a large centrifugal force. The blood and the bubbles separated centrifugally are progressively moved to the radially inner zone while the velocity is markedly reduced. In this zone, a high degree of buoyancy is imparted to the bubbles so that they float and move upwardly, while the blood alone is allowed to enter the lower space 13 throuth the mesh of the filtration member 14. On the other hand, these bubbles of the gas are moved upwardly into the uppermost region of the upper space 12 where the bubble gas accummulates. When a predetermined quantity of gas has accummulated in this uppermost region, the valve 18 is opened so as to relieve the gas from the gas outlet port 17. The valve 18 may be a two-way or three-way cock. Alternatively, the gas outlet port 17 is always kept open to let a small quantity of blood together with the gas pass to equipment such as a cardiotomy reservoir. In FIG. 3, the full-line arrows represent the flow of the blood, while the broken-line arrows represent the flow of the separated bubbles.

As will be understood from the foregoing description, in the described embodiment of the apparatus 10 for removing the bubbles, the blood in which bubbles are suspended is made to form a vortex flow in the vessel 11 so that the bubbles are efficiently separated from the blood by both the centrifugal force in the outer peripheral zone and the axially upward floating force in the central zone. Therefore, the blood in the portion of the upper space 12 around the filtration member 14 is rid of bubbles. With this arrangement, therefore, it is possible to effectively remove fine bubbles of diameters less than 0.1 mm, even when the filtration member 14 is made of a porous material having a comparatively large pore size ranging between 50 and 260 microns, unlike the conventional arrangement in which bubbles are trapped by filtration member. In addition, the described arrangement ensures a high degree of safety and reliability with this apparatus. Furthermore, the use of a filtration member having pore sizes around 260 microns makes it possible to reduce the pressure loss across the filtration member and effectively prevent breakage of structures such as blood platelets, blood cells and so forth.

It is to be noted also that the cylindrical form of the filtration member 14 allows the reading of the filtration member to be reduced for obtaining a given area of mesh, so that the amount of liquid to be used for the priming of the apparatus is decreased advantageously. Since the liquid inlet port 15 is disposed substantially at the same level as the upper end of the filtration member 14, the blood has to travel a long distance after coming through the liquid inlet 15 before going out through the liquid discharge port 16, thereby affording a sufficiently long time for the separation of bubbles. In addition, the entirety of the filtration area of the filtration member 14 can be used equally effectively.

During the operation of the apparatus 10, a large quantity of air may be introduced accidentally, which air stagnates in the center of the vortex flow forming eddy currents of air. Such eddy currents of air, however, are prevented from entering the lower space 13 by the presence of the closure plate affixed to the upper end of the filtration member 14, thereby unfailingly preventing the discharge of the bubbles through the liquid outlet port 16.

Figure 5:
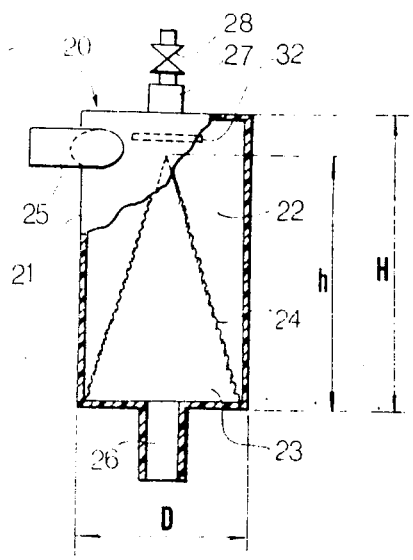
FIG. 5 is a partly-sectioned front elevational view of a second embodiment of the apparatus in accordance with the invention.

FIG. 5 shows an apparatus 20 for removing bubbles from blood, constructed in accordance with a second embodiment of the invention. As in the case of the apparatus 10 of the first embodiment, the apparatus 20 of the second embodiment has a vessel 21, an upper space 22 serving as the liquid inlet space, lower space 23 serving as the liquid outlet space, filtration member 24, liquid inlet port 25, liquid outlet port 26, gas outlet port 27 and a valve 28.

This apparatus 20 is distinguished from the apparatus 10 of the first embodiment by the fact that the filtration member 24 is substantially shaped in a cone with its entire conical surface constituted by a mesh screen. More specifically, as shown in FIG. 6, the conical filtration member 24 is constituted by a conical carrier 29 made of polypropylene and a mesh of polyester fiber having a pore size of 160 microns, formed as a unit with the carrier 29 by an insertion molding. The mesh 30 may be made of a material other than polyester fiber, e.g., fibers of polyamide, polytetrafluoride, polyethylene and so forth. Among these materials, fibers of polyester and polyamide are preferably used because these fibers exhibit only a slight tendency for bubbles to become attached thereto. It is also preferred that the mesh represents a hydrophilic characteristic. So as to meet this demand, it is necessary that the mesh is made of hydrophilic material or made of a material treated beforehand to become hydrophilic. The hydrophilic mesh will easily be wetted by the liquid to prevent the bubbles from becoming attached thereto. The treatment for rendering the mesh hydrophilic can be attained by application of a plasma or by coating with a hydrophilic material such as polyvinylpyrrolidone, polyvinylalcohol, albumin or the like protein, and hydrophilic silicone. A port 31 is formed in the upper end of the conical filtration member 24 so as to provide communication between the upper space 22 and the lower space 23.

The communication port 31 produces a remarkable effect in removing bubbles during priming. Namely, when the mesh of the filtration member 24 is wetted by the blood during priming, a liquid film, i.e., a blood film, is formed on the mesh. Consequently, the air in the filtration member is trapped by and confined in the film on the mesh. The air, however, can be expelled as the blood level is raised and is discharged into the liquid inlet space through the communication port 31 and is perfectly purged through the gas outlet port 17.

The operation and the advantages of the second embodiment are as follows. Namely, in the apparatus 20 of the second embodiment, since the filtration member 24 has a conical form, an ample volume of the upper space 22 is preserved to permit effective separation of bubbles from the blood by centrifugal force. The conical filtration member 24 offers another advantage in that it never impedes the upward flow of the separated bubbles in the central zone of the upper space 22. For these reasons, it is possible to reduce further the outside diameter of the vessel and, hence, the quantity of the priming liquid, in comparison with those of the apparatus 10 of the first embodiment.

The communication port 31 formed in the upper end of the filtration member 24 offers the following advantage. Namely, when residual gas bubbles are found in the lower space below the filtration member 24 after the start of the circulation, the vessel 21 is lightly vibrated while circulating the liquid at a small flow rate so that the residual bubbles are released and float into the upper space through the communication port 31. The priming operation in this way is facilitated. In some cases, a large quantity of gas may be introduced erroneously into the vessel 21. In such case, the gas will produce eddy currents of bubbles in the central region above the filtration member 24. In order to prevent such eddy currents of bubbles from entering the lower space and reaching the liquid outlet port 26, the apparatus 20 of the second enbodiment may be provided with an eddy-current blocking plate 32 above the filtration member, as indicated by the two-dot-and-dash line. The eddy-current blocking plate 32 is preferably inclined slightly so as to prevent stagnation of bubbles which may otherwise occur at the lower side of the eddy-current blocking plate.

The filtration member 24 of the apparatus 20 may accommodate a pillar 33 as shown in FIG. 7. The pillar 33 conveniently reduces the volume of the lower space 23 formed at the lower side of the filtration member 24 thereby decreasing the quantity of liquid required for the priming of the apparatus 20.

FIG. 8 shows a practical example of the apparatus of the invention, intended for use in the separation of bubbles from blood. This apparatus, 40 includes a vessel 41 provided with a liquid inlet port 42, liquid outlet port 43 and a gas outlet port 44. The portion of the vessel 41 defining the liquid inlet section has an increased diameter so as to afford a greater volume to the upper space where the bubbles are separated and so as not to produce any impediment to the upward flow of the bubbles. On the other hand, the diameter of the lower portion of the vessel 41 is minimized because the size of this portion does not materially affect the bubble removing performance.

Figure 9:
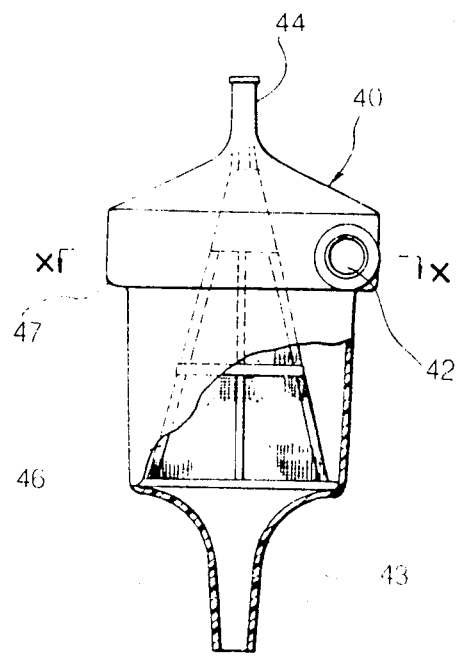
FIG. 9 is a front elevational view illustrating the details of the apparatus shown in FIG. 8.
Figure 10:
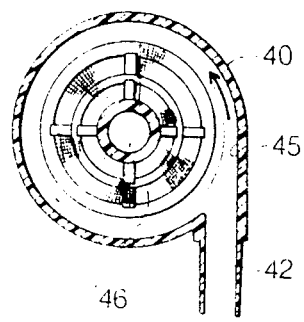
FIG. 10 is a sectional view taken along line X—X in FIG. 9.

FIG. 9 is a front elevational view illustrating the details of the apparatus shown in FIG. 8. FIG. 10 is a sectional view taken along the line X—X in FIG. 9. As will be seen from these drawings, the liquid inlet port 42 of the apparatus 40 opens in the wall 45 of the cylindrical vessel in a tangential direction thereto, at a level near the upper end of the filtration member 24. Therefore, the blood flowing into the upper space 22 through the liquid inlet 42 forms a vortex flow as indicated by the arrows in FIG. 10. Although not shown, it will be clear to those skilled in the art that the apparatus shown in FIGS. 2, 3 and 5 have liquid inlets similar to that shown in FIGS. 9 and 10.

Figure 1:
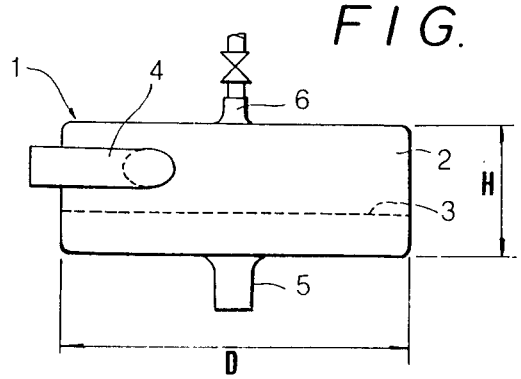
FIG. 1 is a front elevational view of a conventional apparatus for removing bubbles from a liquid.

Table 1 shown the sizes of major parts of the apparatus 10 and 20 of the invention shown in FIGS. 2 and 5, as well as the quantities of the priming liquid and the values of pressure loss, in comparison with those of the conventional apparatus 1 shown in FIG. 1. From this table, it will be understood that the quantity of the priming liquid and the pressure loss are much decreased in the apparatus 10 and 20 of the invention, as compared with those of the conventional apparatus 1.

TABLE 1

| type of apparatus | 1 | 10 | 20 |
|---|---|---|---|
| D (cm) | 8 | 6 | 4.5 |
| H (cm) | 3.5 | 4.3 | 7.5 |
| d (cm) | — | 4.5 | 4.5 |
| h (cm) | — | 3.5 | 6.5 |
| priming volume (ml) | 175 | 150 | 120 |
| pressure loss (mmHg) | 45 | 35 | 30 |

(value of pressure loss measured with water of 25° C. at flow rate of 6 liters per min.)

As has been described, the present invention basically provides an apparatus for removing bubbles from a liquid comprising: a vessel; a filtration member disposed in the vessel and dividing the space in the vessel into a liquid inlet space and a liquid outlet space; a liquid inlet port formed in the wall of the vessel in communication with the liquid inlet space and adapted to introduce a liquid into the liquid inlet space in the form of a vortex flow around the axis of the vessel; a liquid outlet port formed in the wall of the vessel in communication with the liquid outlet space and adapted to allow the treated liquid passed through the filtration member to be discharged therethrough; and a gas outlet port formed in the wall of the vessel in communication with the uppermost region of the liquid inlet space and adapted to allow the gas of the separated bubbles to be discharged therethrough; wherein the filtration member is a three dimensional structure disposed in the vessel coaxially therewith, the upper end of the filtration member being positioned at the same level as the liquid inlet port.

With this arrangement, it is possible to satisfactorily remove bubbles from a liquid such as blood, while reducing the pressure loss of the liquid across the filtration member and reducing the quantity of the liquid required for priming.

According to one embodiment of the invention in which the filtration member is made of hydrophilic material or is treated to become hydrophilic, it is possible to prevent bubbles from becoming attached to the filtration member to eliminate any dead area on the same.

In another embodiment of the invention employing a conical filtration member, an ample volume is preserved for the upper space between the vessel wall and the filtration member, thereby allowing efficient separation of the bubbles and smooth upward flow of the separated bubbles without any impediment. Consequently, the outside diameter of the vessel can be decreased to reduce the quantity of the liquid necessary for priming.

In still another embodiment of the invention, a communication port is formed in the upper end of the filtration member to provide communication between the liquid inlet space and the liquid outlet space. Through this communication port, any residual bubbles in the liquid outlet space or attached to the lower surface of the filtration member are released into the liquid inlet space so that the priming operation is considerably facilitated.

According to a further embodiment of the invention, an eddy-current blocking plate is provided on or above the top of the filtration member. This arrangement effectively prevents eddy currents of bubbles formed when a large quantity of gas is accidentally introduced into the vessel from reaching the liquid outlet port through the liquid outlet space below the filtration member.

As many apparently widely different embodiments of the present invention can be made without departing from the spirit and scope thereof, it is to be understood that the invention is not limited to the specific embodiments thereof except as defined in the appended claims.

What is claimed is:

1. An apparatus for removing bubbles from a liquid, comprising:
    a generally cylindrical vessel having an axis and a cylindrical inner wall;
    a substantially conically shaped filtration member disposed in said vessel coaxially therewith, said filtration member dividing the space in said vessel into a liquid inlet space and a liquid outlet space;
    a liquid inlet port formed in a wall of said vessel in communication with said liquid inlet space for introducing a liquid into said liquid inelt space in the form of a vortex flow around the axis of said vessel;
    a liquid outlet port formed in the wall of said vessel in communication with said liquid outlet space for adapting the treated liquid passed through said filtration member to be discharged therethrough; and
    a gas outlet port formed in the wall of said vessel in communication with an uppermost region of said liquid inlet space for allowing the gas of the separated bubbles to be discharged therethrough;
    said filtration member having an upper apex end and a bottom end, said upper apex end being positioned at substantially the same level as said liquid inlet port, the filtration area of said filtration member being reduced in the vicinity of its upper apex end and increasing in the axial direction toward said bottom end of asid filtration member in accordance with its conical configuration, and the radial separation between the periphery of said filtration member and said inner wall of said vessel increasing in the axial direction thereof from said bottom end toward sasid upper apex end by an amount sufficient to allow separation of bubbles from said vortex flow of said liquid in said liquid inlet space.

2. An apparatus according to claim 1, wherein said filtration member is made of a porous material having a pore size ranging between 50 and 260 microns.

3. An apparatus according to claim 1, wherein said filtration member is made of a hydrophilic material.

4. An apparatus according to claim 1, wherein said filtration member is made of porous material treated beforehand to become hydrophilic.

5. An apparatus according to claim 1, wherein a pillar is provided in the conically shaped filtration member for reducing the liquid volume thereof.

6. An apparatus according to claim 1, wherein said filtration member of substantially conical shape is provided at its upper end with a communication port which provides communication between said liquid inlet space and said liquid outlet space.

7. An apparatus according to claim 1, wherein said filtration member of substantially conical shape is provided over the upper apex end thereof with an eddy-current blocking plate which prevents eddy currents of bubbles formed thereon from entering said liquid outlet space.

* * * * *

UNITED STATES PATENT AND TRADEMARK OFFICE
CERTIFICATE OF CORRECTION

PATENT NO. : 4,690,762

DATED : September 1, 1987

INVENTOR(S) : Y. KATSURA

It is certified that error appears in the above-identified patent and that said Letters Patent is hereby corrected as shown below:

Column 5, line 7, "by filtration" should read
-- by the filtration --.

Column 6, line 60, "apparatus, 40" should read
-- apparatus 40 --.

Column 8, line 63, "sasid" should read -- said --.

Signed and Sealed this

Fifth Day of April, 1988

*Attest:*

DONALD J. QUIGG

*Attesting Officer*       *Commissioner of Patents and Trademarks*